(12) United States Patent
Matula et al.

(10) Patent No.: US 7,033,328 B2
(45) Date of Patent: Apr. 25, 2006

(54) DIRECT WAVE CAVITATION SUPPRESSOR FOR FOCUSED SHOCK-WAVE DEVICES

(75) Inventors: Thomas J. Matula, Kirkland, WA (US); Paul Hilmo, Phoenix, AZ (US); Michael Bailey, Seattle, WA (US)

(73) Assignee: University of Washington, Seattle, WA (US)

( * ) Notice: Subject to any disclaimer, the term of this patent is extended or adjusted under 35 U.S.C. 154(b) by 314 days.

(21) Appl. No.: 10/266,874

(22) Filed: Oct. 8, 2002

(65) Prior Publication Data

US 2004/0068206 A1 Apr. 8, 2004

(51) Int. Cl.
*A61B 17/22* (2006.01)
(52) U.S. Cl. .............................. 601/2; 601/4
(58) Field of Classification Search ............ 601/2–4; 367/141, 147, 151; 600/439
See application file for complete search history.

(56) References Cited

U.S. PATENT DOCUMENTS 4,702,249 A * 10/1987 de la Fonteijne ............ 601/4
4,844,081 A * 7/1989 Northeved et al. ......... 600/439
5,209,222 A * 5/1993 Viebach et al. ............. 601/4

* cited by examiner

*Primary Examiner*—Ruth S. Smith
(74) *Attorney, Agent, or Firm*—Christensen O'Connor Johnson Kindness PLLC

(57) ABSTRACT

A reflector (14) reflects energy emitting from an energy source (16) and focuses and directs it to a target. An aperture stop or suppressor disk (18) is positioned between the energy source (16) and target. The outer periphery of the aperture stop or suppressor disk (18) is an irregular curve (FIGS. 12 and 13). This shape of the periphery prevents diffraction enhancement to the direct wave.

8 Claims, 8 Drawing Sheets

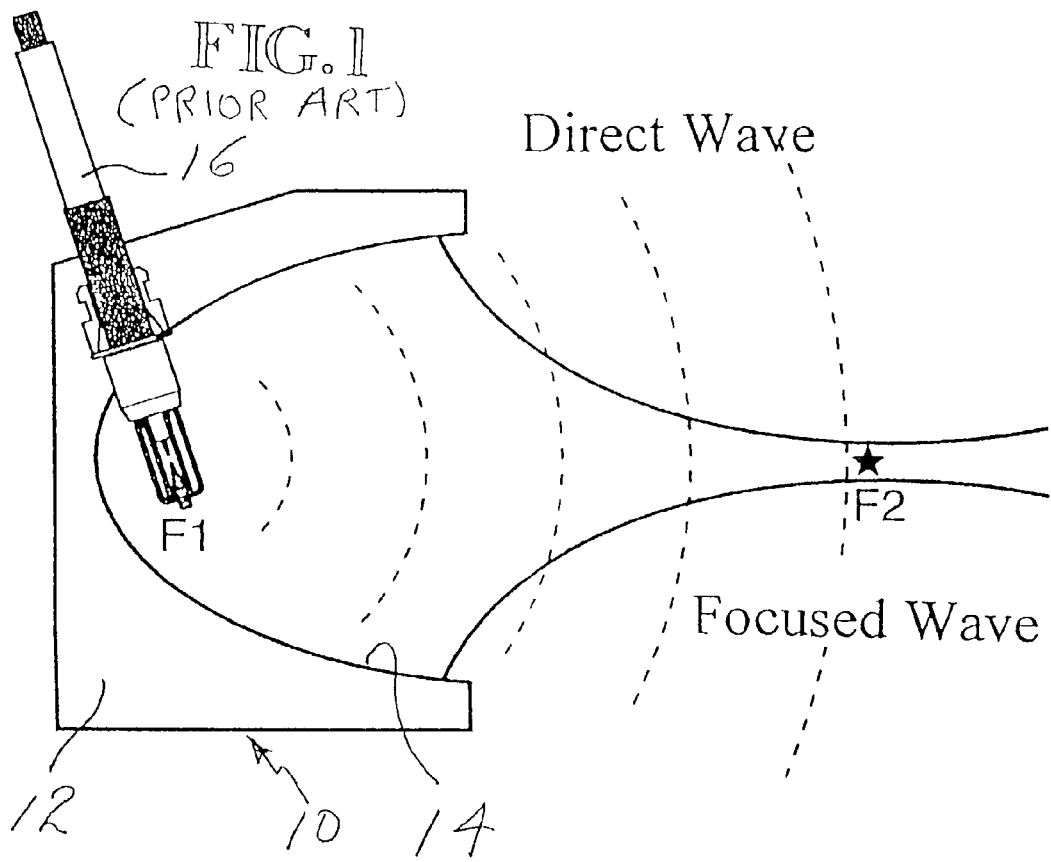
FIG. 1 (PRIOR ART)
FIG. 2
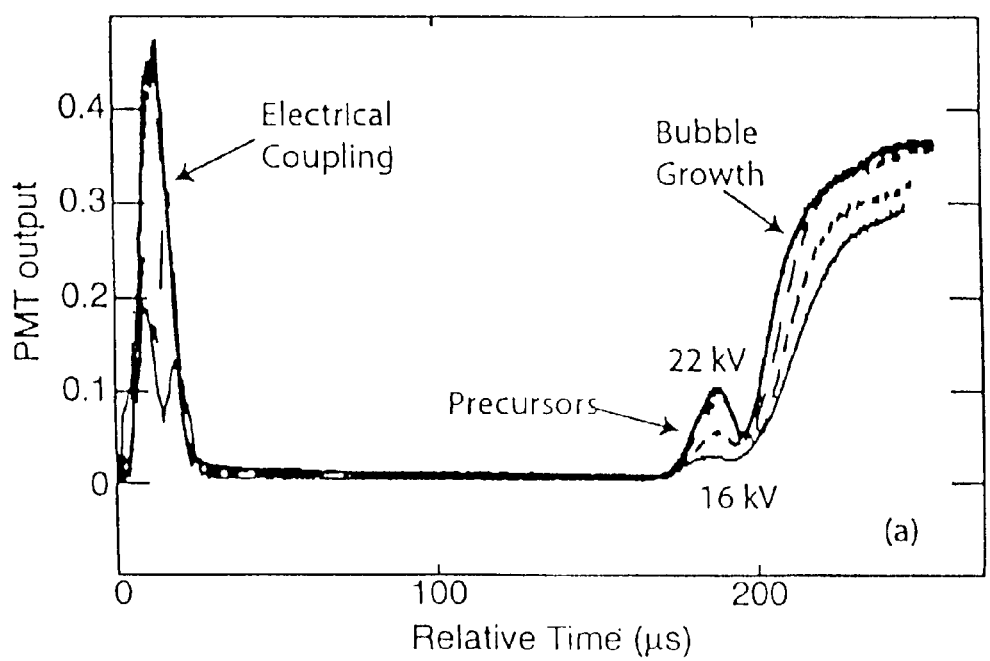

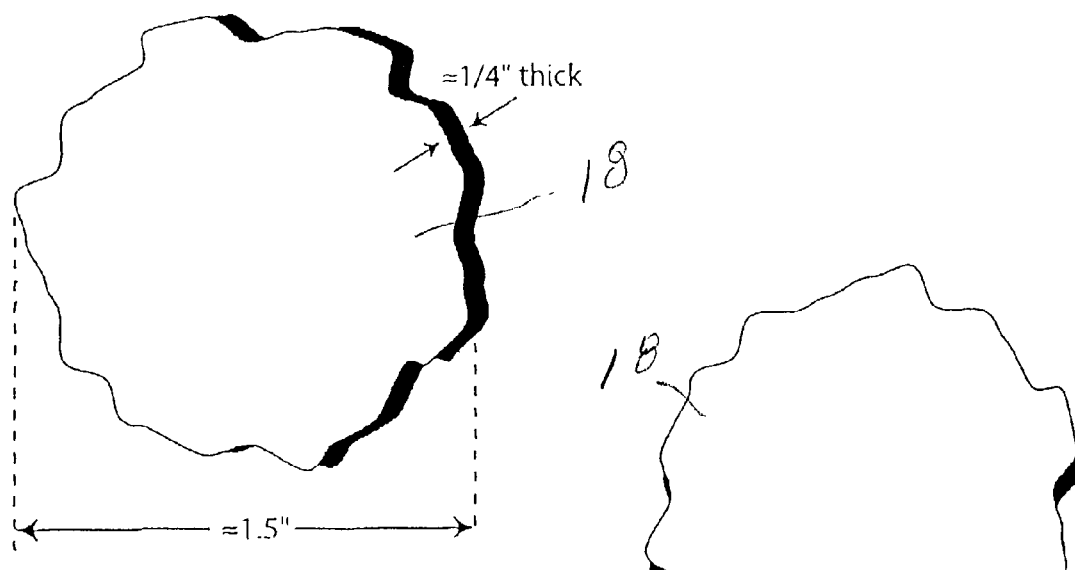
FIG. 12
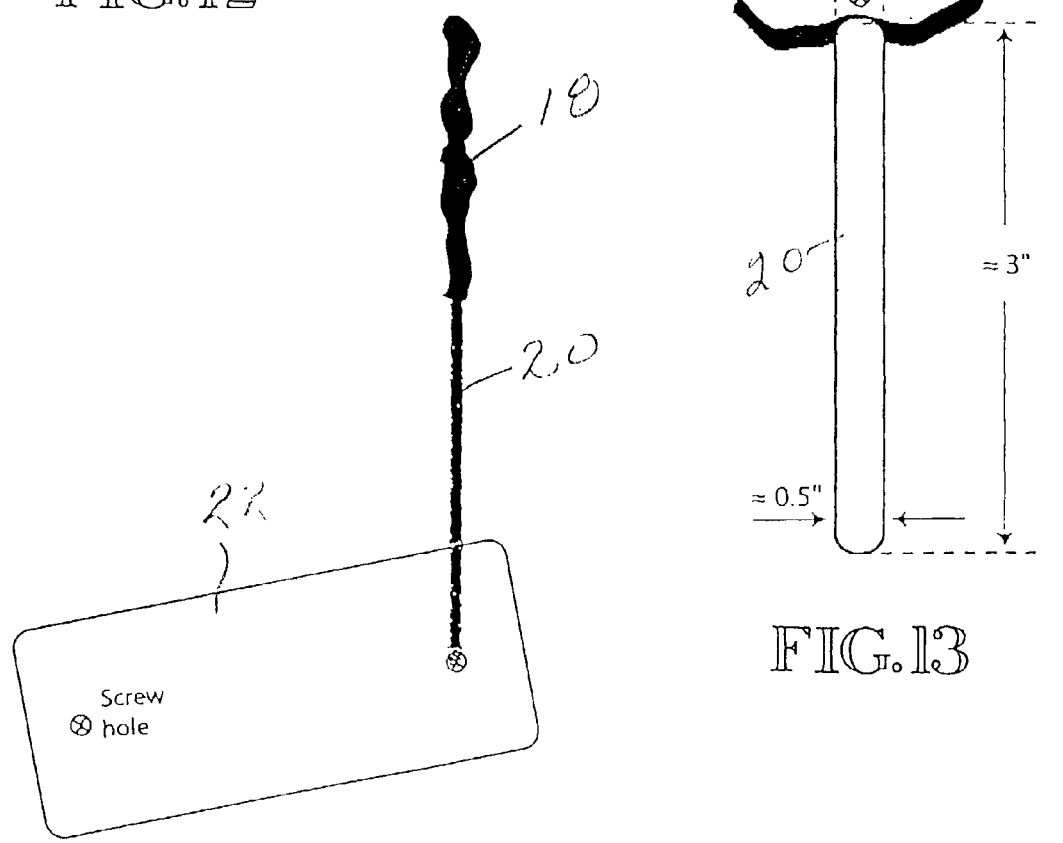
FIG. 13
FIG. 14

DIRECT WAVE CAVITATION SUPPRESSOR FOR FOCUSED SHOCK-WAVE DEVICES

The subject invention was made under DARPA contract no. N00014-99-1-0793, managed by ONR, and developed under NIH grant P01 DK 43881-09.

TECHNICAL FIELD

This invention relates to shock-wave focusing devices, e.g. electrohydraulic and electromagnetic lithotripters. More particularly, it relates to a method and apparatus for making the focused shock-wave more efficient, enabling it to perform its function in a shorter period of time.

BACKGROUND OF THE INVENTION

Shock-wave devices are commonly used clinically for therapeutic treatment. For example, an electrohydraulic shock-wave lithotripter is a device that generates a focused shock-wave and directs it onto a clinical target, such as a kidney stone. An electrohydraulic shock-wave lithotripter is only one example of the shock-wave devices that can benefit from the present invention. This device is characterized by a focusing reflector having spaced-apart first and second foci. A shock-wave generator is positioned substantially at the first foci and is adapted to discharge shock-wave creating energy outwardly from itself to the focusing reflector. The focusing reflector is configured to receive shock-wave energy and focus it and direct it as a focused wave to a target (e.g. kidney stone) at the second foci.

One use of a shock-wave focusing device is to fragment kidney stones into small pieces that can then be safely removed from a patient via the urinary tract. There is evidence that normal tissue can at the same time be damaged.

Several thousand shock-wave generations are necessary to fragment a kidney stone. The clinician takes care to operate the lithotripter at the highest safe rate of operation. Currently, the instrument is operated typically at 0.5–2.0 Hz pulse repetition frequency (PRF). There is a need to decrease the total number of shock-waves that are delivered to the kidney stone to cause its comminution, in order to reduce the unwanted and unhealthy bioeffects on healthy tissue.

A principal object of the present invention is to increase the efficiency of a focused shock-wave device so that it can perform its function satisfactorily by use of a reduced number of focused shock-waves or by an increased PRF.

BRIEF SUMMARY OF THE INVENTION

The invention includes the discovery that the effectiveness of focused shock-waves is decreased by direct waves emanating from the shock-wave generator. The shock-waves diverge spherically from the shock-wave generator. Those shock-waves that strike the focusing reflector are focused by the reflector to form the focused shock-wave that is then directed to a target, e.g. a kidney stone. The direct waves are those shock-waves that miss the reflector and move directly to the target. It has been observed that direct waves cause a premature growth of preexisting bubbles on and near the target. These bubbles can act as a protective membrane around the region of target, decreasing the efficiency of the focused shock-wave. It has been discovered, by removing or decreasing the effect of the direct wave, premature bubble growth is reduced.

The present invention is basically characterized by providing a direct-wave cavitation suppressor and positioning it between the first and second foci of the focusing reflector, in a position to block direct shock-waves from traveling from the shock-wave generator directly to the second foci. The direct-wave cavitation suppressor has a periphery spaced inwardly from the focusing reflector. The outer periphery is shaped to substantially prevent diffraction enhancement of the direct waves as it moves around the direct-wave cavitation suppressor.

Typically, the focusing reflector includes a reflecting surfaces of at least near elliptical shape. Typically also, the shock-wave generator is an electric spark discharge device. In preferred form, the direct-wave cavitation suppressor is generally in the form of a disk having an irregular periphery.

Another aspect of the invention is to provide a method of producing a focused shock-wave and delivering it to an object. This method is basically characterized by providing a shock-wave generator and a focusing reflector positioned to direct a focused shock wave on an object. A direct-wave cavitation suppressor is positioned between the generator and object in a position to block direct waves from traveling directly from the generator to the object. The shock-wave generator is operated to discharge shock-wave creating energy outwardly from itself. The focusing reflector is used to receive shock-wave energy and focus it and direct it as a focused wave on the object. The direct-wave cavitation suppressor is configured to substantially block the direct shock waves from traveling directly to the object. The direct-wave cavitation suppressor is also configured to prevent diffraction enhancement of the direct waves as they move around the direct-wave cavitation suppressor. In preferred form, the direct-wave cavitation suppressor is generally in the shape of a disk having an irregular periphery. In one form, the focusing reflector is shaped substantially like an end portion of an ellipse. An electrical spark discharge device or an electromagnetic generator is used for the shock-wave generator.

Other objects, advantages and features of the invention will become apparent from the description of the best mode set forth below, from the drawings, from the claims and from the principles that are embodied in the specific structures that are illustrated and described.

BRIEF DESCRIPTION OF THE SEVERAL VIEWS OF THE DRAWING

Like reference numerals are used to designate like parts throughout the several views of the drawings, and:

FIG. 1 is a diagram of a shock-wave lithotripter that is in the public domain, such view showing a shock-wave generator and its relationship to a truncated ellipsoidal reflector, direct and focused shock-waves and a second foci at which the focused wave is directed;

FIG. 2 is a plot of light-scattered signal level versus relative time, such graph showing the influence of the direct wave precursor on preexisting bubbles that respond to the direct wave before the main shockwave arrives at the second foci;

FIG. 12 is a view taken substantially along line 12—12 of FIG. 15, but with the suppressor disk tilted somewhat to show the thickness dimension of the suppressor disk;

FIG. 13 is a view similar to FIG. 12, but with a support arm added to the suppressor disk and with the suppressor disk and the support arm rotated forwardly from the lower end of the support arm from a true elevational view;

FIG. 14 is a side view of the suppressor disk and support arm shown by FIG. 13, showing the lower end of the support arm connected to a support member which includes a screw hole for receiving a screw that is used to adjustably mount it onto a housing portion of the shock-wave lithotripter;

DETAILED DESCRIPTION OF THE INVENTION

Figure 9:
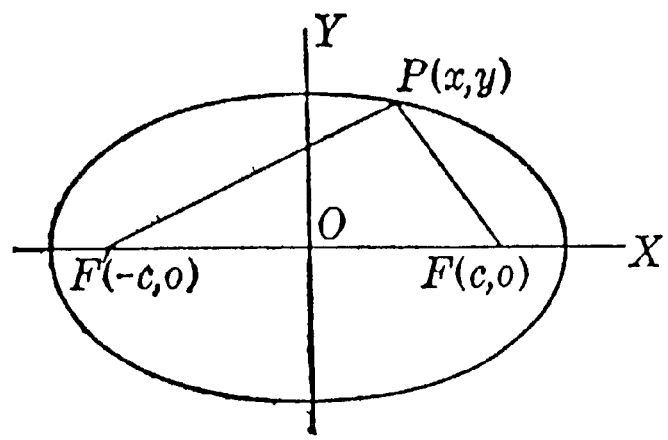
FIG. 9 is a diagram of a true ellipse, showing that an ellipse is the locus of a point the sum of whose undirected distances from two fixed points equals a constant, wherein the two fixed points are the foci or focal points of the ellipse.

FIG. 1 is a schematic diagram of a prior art lithotripter 10. It comprises a body 12 formed to provide a focusing reflector 14 and mounts a spark discharge device 16. The focusing surface 14 is an end portion of an ellipsoid or has a curvature that will perform substantially like an elliptical reflector. For background purposes, FIG. 9 is a diagram of a true ellipse. By definition, an ellipse is the locus of a point the sum of whose undirected distances from two fixed points equals a constant. The two fixed points are the foci F (−c, 0) and F (c, 0). The midpoint of the segment joining the foci is the center and the line through them is the principal axis of the ellipse. The distance F (−c, 0) P (x, y) added to the distance P (x, y) F (c, 0) is a constant for all points P (x, y) on the ellipse. The important feature of the ellipse to the present invention is that if the ellipse is three-dimensional, viz. ellipsoidal, energy extending from F (−c, 0) to P (x, y) would be reflected by the ellipsoid to F (c, 0). The same is true in the opposite direction. Energy traveling from F (c, 0) to P (x, y) would be reflected by the ellipsoid to F (−c, 0).

Referring to FIG. 1, the surface 14 is the frustum of an ellipsoid, or a surface that is similar enough to have two foci F1, F2. Herein the terms "ellipse" and "ellipsoid" are used to mean both a true ellipse and a true ellipsoid and other curves that are substantially similar enough to the true curves that they will have two foci and will behave the same when used in a focused-wave device.

The device shown by FIG. 1 is submerged in a fluid. The shock-wave generator is positioned to provide a spark discharge at F1. It functions as a shock-wave generator at the first foci F1. The generated shock-wave energy will radiate from foci F1. The portion of this energy that moves out to and contacts the surface 14 will be reflected by the surface 14 and sent on a focused path onto loci F2. This reflected energy forms what is referred to as the "focused wave." The envelope of this wave is shown by solid lines in FIG. 1. Some of the shock-wave energy never strikes the surface 14. This energy moves away from foci F1 towards foci F2. This energy is referred to herein as the "direct wave." In FIG. 1 the direct wave is shown by a succession of dashed wave front lines. As shown by FIG. 1, the center region of the direct wave, if left alone, as is the case in the prior art devices, will travel directly to foci F2. In a shock-wave lithotripter, a target object is located substantially at foci F2. By way of typical and therefore non-limitive example, the target may be kidney stones in a person.

In lithotripsy, the intense shock waves, over the course of a few thousand shocks, fragment the kidney stone into small pieces that can be safely removed via the urinary tract. Because several thousand shocks are necessary, the clinician usually operates the instrument at the highest safe rate of operation, the pulse repetition frequency (PRF). Current modes of operation are typically 0.5–2.0 Hz PRF.

In addition to fragmenting the kidney stone, there is evidence that normal tissue is also damaged by the shock-waves. For this reason, electrohydraulic lithotripters are limited in use. There is a current need to decrease the total number of shocks for kidney stone comminution, to reduce the unhealthy bioeffects on healthy tissue.

The leading direct wave is usually considered to be much smaller in amplitude than the focused wave. However, we have observed its influence on the target substantially at F2 by using light-scattering techniques. We have found that the direct wave causes the premature growth of preexisting bubbles on and near the region of interest, viz. the kidney stone or stones, substantially at F2. These bubbles can act as a protective membrane around the region of interest, viz. the kidney stone, decreasing the efficiency of the focused wave. FIG. 2 shows the influence of the direct wave on preexisting bubbles. The preexisting bubbles respond to the direct wave before the focused wave arrives. Because of this interaction, the bubbles grow and can shield the region of interest from the focused wave. By removing or decreasing the effect of the direct wave, the focused wave will be more efficient, leading to shorter clinical procedures.

Electrohydraulic lithotripters generate a shock wave at the focus that can be modeled with the following equation:

$$P(t)=2P_a e^{-\alpha t} \cos(\omega t+\pi/3). \tag{1}$$

In our models we use $\alpha=3.5\times10^5$ for the decay constant of the positive pressure spike, and $f=50$ kHz for defining the negative tail. Because bubble dynamics, especially the explosive growth, is not governed by the positive pressure spike, we neglect the finite rise-time of the spike, and assume is occurs instantaneously.

The shock wave described by Eq. 1 results from an underwater spark discharge from one foci F1 of an ellipsoid that is then focused by a truncated ellipsoidal reflector to the other foci F2. At F2, this shock wave pressure amplitude is about 30 Mpa. See Cleveland, R. O., et al., *Design and characterization of a research electrohydraulic lithotripter patterned after the Dornier HM3*. Review of Scientific Instruments, 2000. 71 (6): p. 2514–2525. There is also the direct spherically expanding wave that passes directly from F1 to F2. Although smaller in amplitude, the peak amplitude can be greater than 1 Mpa. See Coleman, A. J., et al., *Pressure waveforms generated by a Dornier extra-corporeal shock-wave lithotripter*. Ultrasound Med Biol, 1987. 13: p. 651–657.

Figure 3:
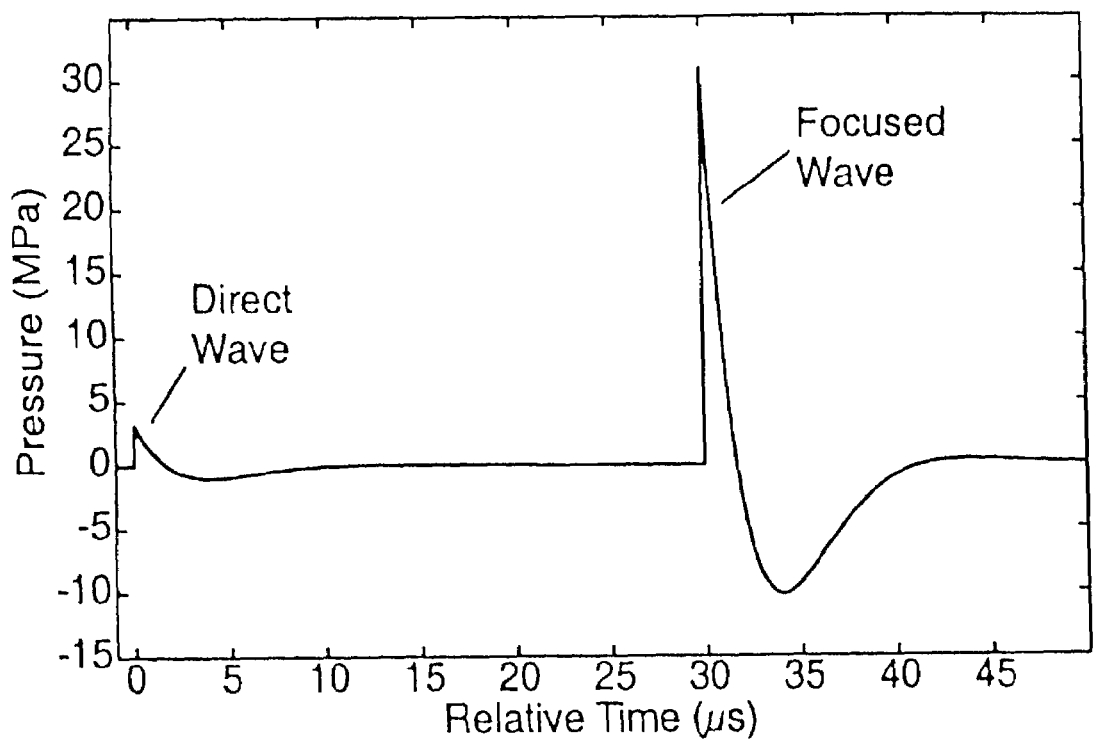
FIG. 3 is a numerical simulation of the relative amplitude and timing of the direct and focused waves.
Figure 7:
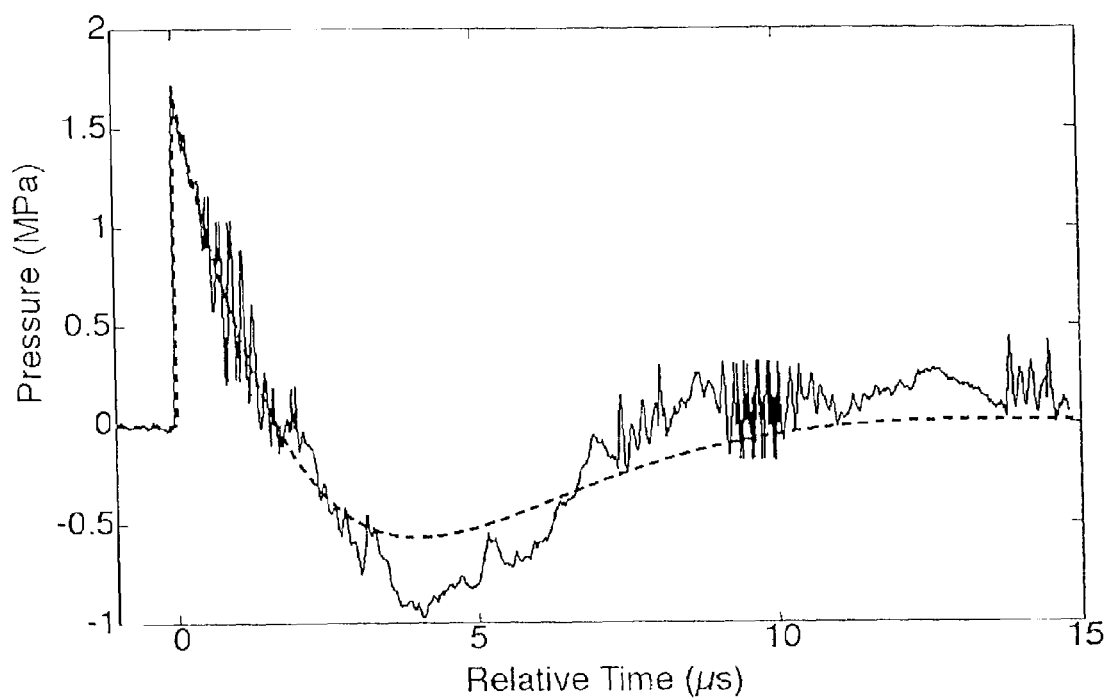
FIG. 7 is a plot of the hydro-phone detected direct wave at F2 and a numerical simulation of the direct wave.

The direct wave, with a negative tail of sufficient amplitude, can affect preexisting bubbles at F2. Because of the geometric location of the sparker, the direct wave precedes the focused wave by approximately 30 µs. In our model we assume for simplicity that the direct wave has the same shape as that given by Eq. 1, with reduced amplitude, and that it precedes the focused wave by 30 µs. This is shown by FIG. 3 in which the focused shock wave from the spark discharge is modeled as shown in Eq. 1. For simplicity, we also assume that the direct wave has a similar form, but at a reduced amplitude factor. Evidence that supports our assumption is shown in FIG. 7. For this figure, the reduction factor is 10.

Corresponding bubble dynamics from such a wave were calculated using the Gilmore equation. The equation was solved for an initial bubble radius of 5 µm. Other parameters were taken from the literature. See in particular Church, C. C., *A theoretical study of cavitation generated by an extracorporeal shock wave lithotripter*. J. Acoust. Soc. Am., 1989. 86: p. 215–227. For this work, we did not include gas diffusion.

Figure 4:
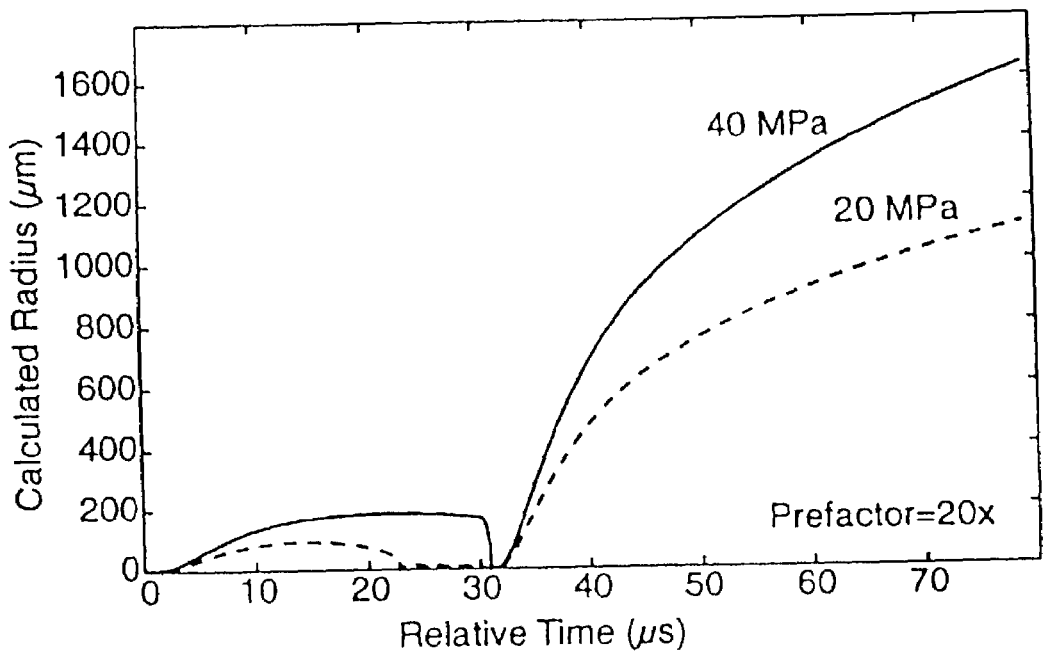
FIG. 4 is a plot of bubble radius versus relative time based on an assumed direct wave amplitude that is a factor of 20× smaller than the focused wave amplitude.
Figure 5:
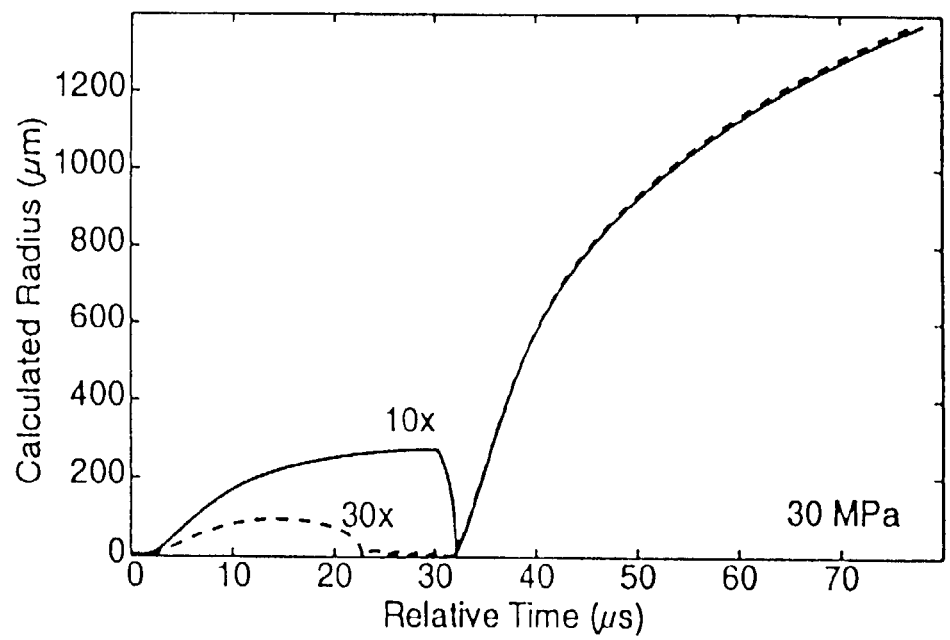
FIG. 5 is a graph like FIG. 4 but showing the effect of changing the direct wave prefactor, such view showing a 10× prefactor and a 30× prefactor.

We show in FIGS. 4 and 5 examples of bubble dynamics resulting from the direct wave preceding the focused wave. FIG. 4 shows calculated bubble dynamics for the lithotripter pulse from FIG. 3. The calculations were for peak pressures ($P_a$) of 20, and 40 Mpa, from the focused wave. As the pressure amplitude increases, bubble growth from the direct wave also increases. The effect of the pre-factor used to determine the amplitude of the direct wave is shown in FIG. 5. For a given peak positive pressure, the bubble growth from the direct wave depends on the prefactor used. The negative tail associated with the direct wave causes preexisting bubbles to grow. The duration of this growth stage depends on the pressure amplitude and the relative amplitude of the direct wave. In FIG. 4, where we have assumed that the direct wave amplitude is a factor of 20× smaller than the focused wave, bubble expansion increases with pressure amplitude. For higher pressures, an asymmetry occurs (near t=30 µs) when the incident focused wave forces the growing bubble to collapse. In FIG. 5, we show the effect of changing the direct wave prefactor (amplitude reduction factor). Shown are a 10× prefactor and a 30× prefactor. Bubble expansion from the direct wave is dependent on the prefactor, as expected.

Figure 6:
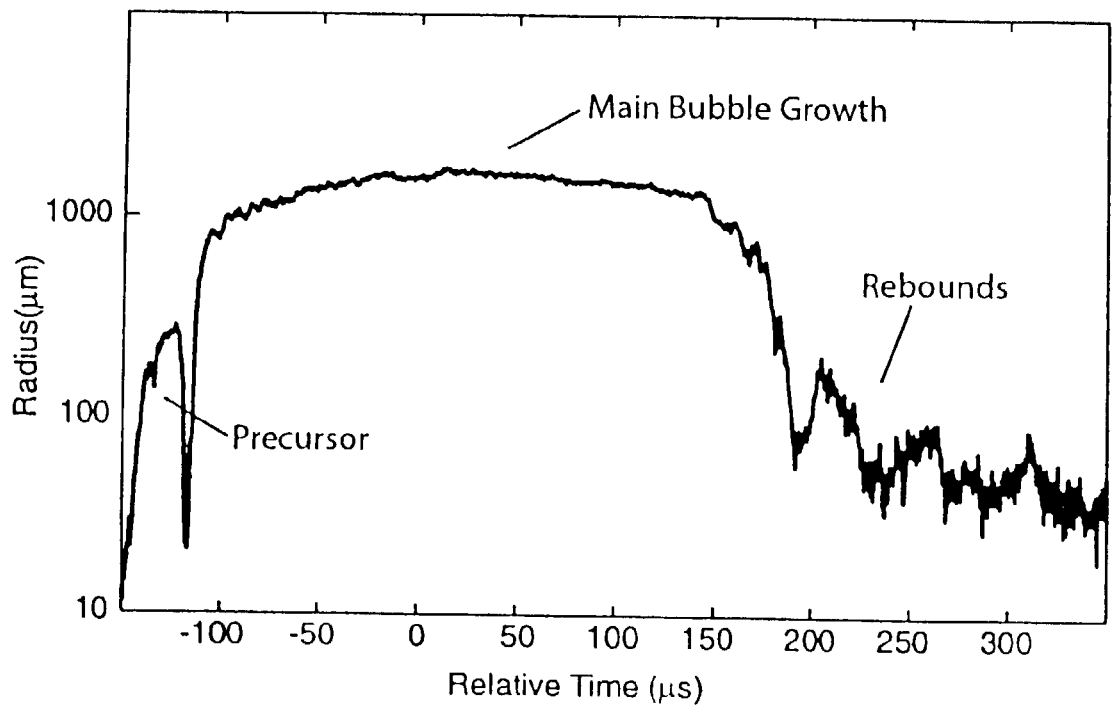
FIG. 6 is another graph plotting experimentally measured bubble radius versus relative time, such graph showing a precursor signal corresponding to bubble growth due to the direct wave.
Figure 8:
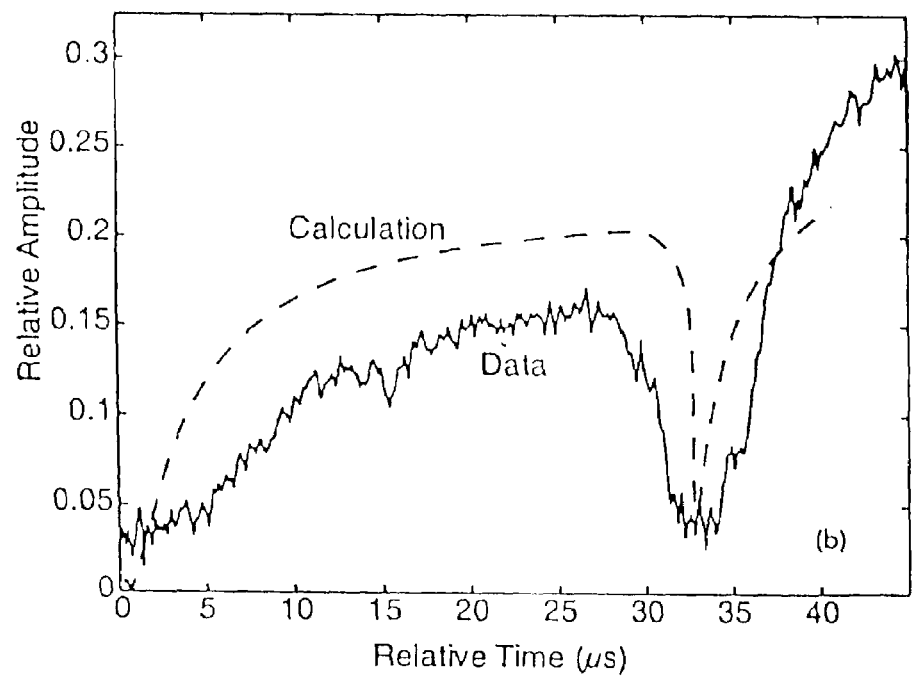
FIG. 8 is a plot of precursor amplitude versus relative time and a comparison with a numerical simulation.

FIG. 6 shows an example of bubble dynamics associated with lithotripsy. The precursor signal corresponds to bubble growth due to the direct wave. The experimental system is described in detail in Matula, T. J., *Radial response of individual bubbles subjected to shock wave lithotripsy pulses in vitro*. Physics of fluids, 2002. 104: 913–921. Essentially, a laser beam passing through a water-filled chamber placed at the lithotripter focus scatters off bubbles, and the scattered light is focused onto a photomultiplier tube (PMT). The resulting signal depends on the bubble size— larger bubbles scatter more light (in this context). An example of such a signal is shown in FIG. 6. Here, the focused wave is incident near t=−120 µs. The bubble collapses near t=180 µs. There is also a relatively large precursor signal. This signal is due to one or more bubbles growing after the direct wave passes through Referring to FIG. 7, the main bubble growth from the lithotripter pulse is preceded by a precursor. The precursor signal, due to bubble growth from the direct wave, depends on sparker voltage. Higher spark voltages result in an increased growth of preexisting bubbles. FIG. 8 presents a qualitative comparison of the asymmetries observed with the direct wave bubble and the calculation. Bubble growth from the direct wave can be halted when the focused wave arrives.

The amplitude of the precursor signal depends on the applied voltage. Larger signals are observed with higher spark discharge voltages. FIG. 7 shows this effect. There is an initial large transient signal corresponding to electrical coupling when the sparker discharges. The distance between the sparker and F2 is about 228 millimeters, corresponding to a delay time of about 150 µs. The focused wave delay time is about 180 µs. The main bubble growth resulting from the focused wave is truncated so that we can focus on the direct wave influence. As the voltage is increased from 16 kV to 22 kV, the amplitude of the precursor—the direct wave bubble—increases.

A qualitative comparison between the model and the experiment is shown in FIG. 8. Here we show the similarity in the asymmetry of bubble growth and collapse due to the direct wave. The collapse is due to the arrival of the focused shock wave, causing the bubble to be compressed. No attempt was made to fit the calculation with the data. Not all experiments (or calculations) show such an asymmetry. Bubble growth must be sufficiently long so that the focused wave can initiate the collapse. For smaller spark voltages, inertial bubble collapse may occur before the focused wave arrives.

We have shown evidence of bubble dynamics associated with the direct wave. Although the direct wave is much smaller in amplitude than the focused wave, it is still sufficiently large to affect preexisting bubbles. Bubble growth due to the direct wave must be due to a negative pressure, even though most explosion models only account for the positive spike. In our model, we assume the direct wave is a miniature version of the focused wave; FIG. 7 confirms this. Bubble growth due to the direct wave depends on the sparker voltage. At high voltages, we observe an asymmetry that corresponds to the arrival of the focused wave when the bubble is still relatively large.

As a final observation, we inserted an aperture stop, essentially a disk, near the sparker, so that it can block the direct wave. When inserted, hydrophone measurements of the direct wave disappear, as do bubble dynamics associated with the direct wave.

Figure 10:
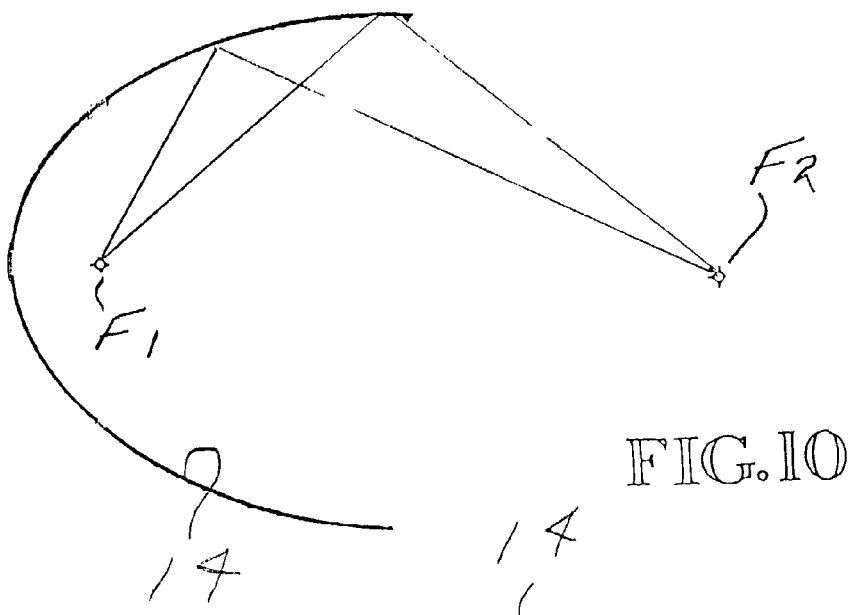
FIG. 10 is a diagram of a truncated ellipse showing both foci, and including two lines extending outwardly from the first foci to the truncated ellipse and reflecting from a contacting point on the ellipse to the second foci, such view being a geometric diagram of the shock-wave lithotripter shown by FIG. 1, minus the direct and focused waves.
Figure 11:
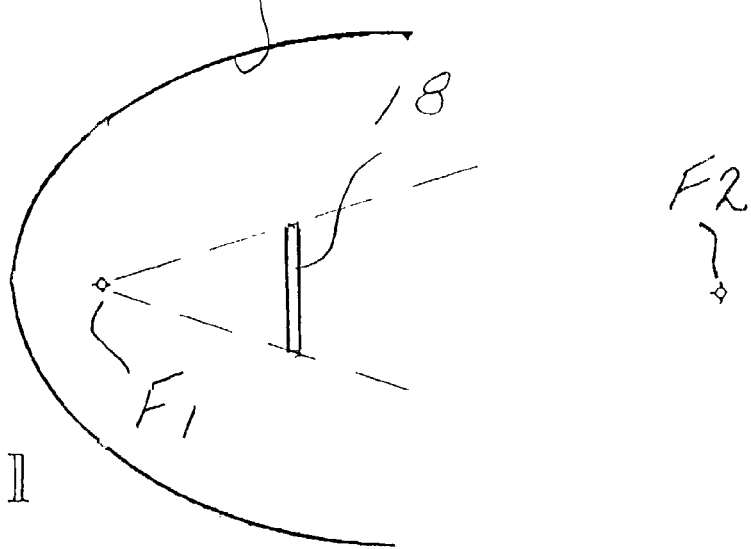
FIG. 11 is a diagram like FIG. 10 but including the direct wave cavitation suppressor of the present invention minus structural detail.

FIG. 10 shows examples of the energy that contacts the ellipsoidal reflector and is focused by it and directed onto the foci F2. FIG. 11 is like FIG. 10 but it shows an aperture stop 18 positioned between the foci F1, F2. The aperture stop 18 is also herein referred to as a suppressor disk.

The preferred implementation of the invention is described as follows:

An irregularly-shaped aperture stop 18 (suppressor disk) of approximately 1.5-inch diameter is machined out of metal, plastic, rubber, or other material (see FIG. 12). The device should be somewhat "disk-shaped", but with sufficient surface contours to prevent diffraction enhancements to the outgoing wave. It is important that diffraction not focus the outgoing wave.

Figure 16:
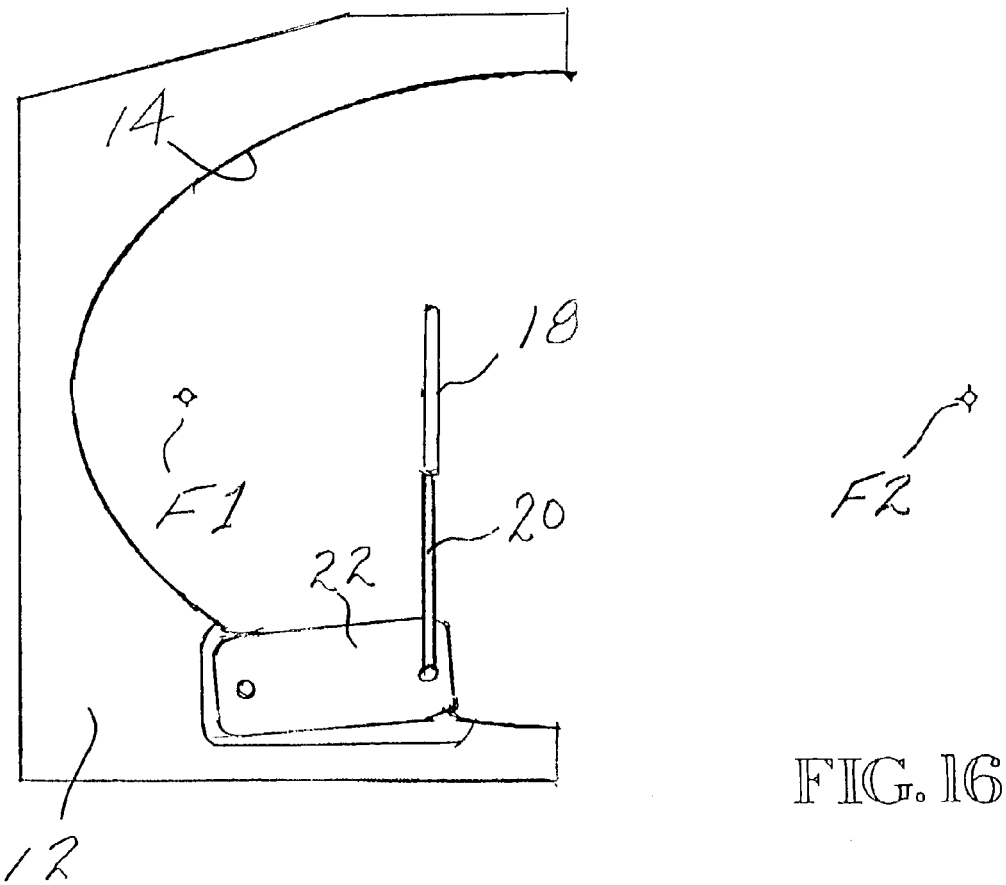
FIG. 16 is a view like FIG. 15 but showing the disk mounting structure that is illustrated by itself in FIG. 14 added to the reflector housing.

In one embodiment, the disk edge is mounted to a metal or plastic rod 20, as shown in FIG. 13. The rod, in turn, is mounted to a moveable plate 22, shown in FIG. 14. The plate is secured to the bottom of the reflector such that the direct wave is blocked (FIG. 16).

Figure 17:
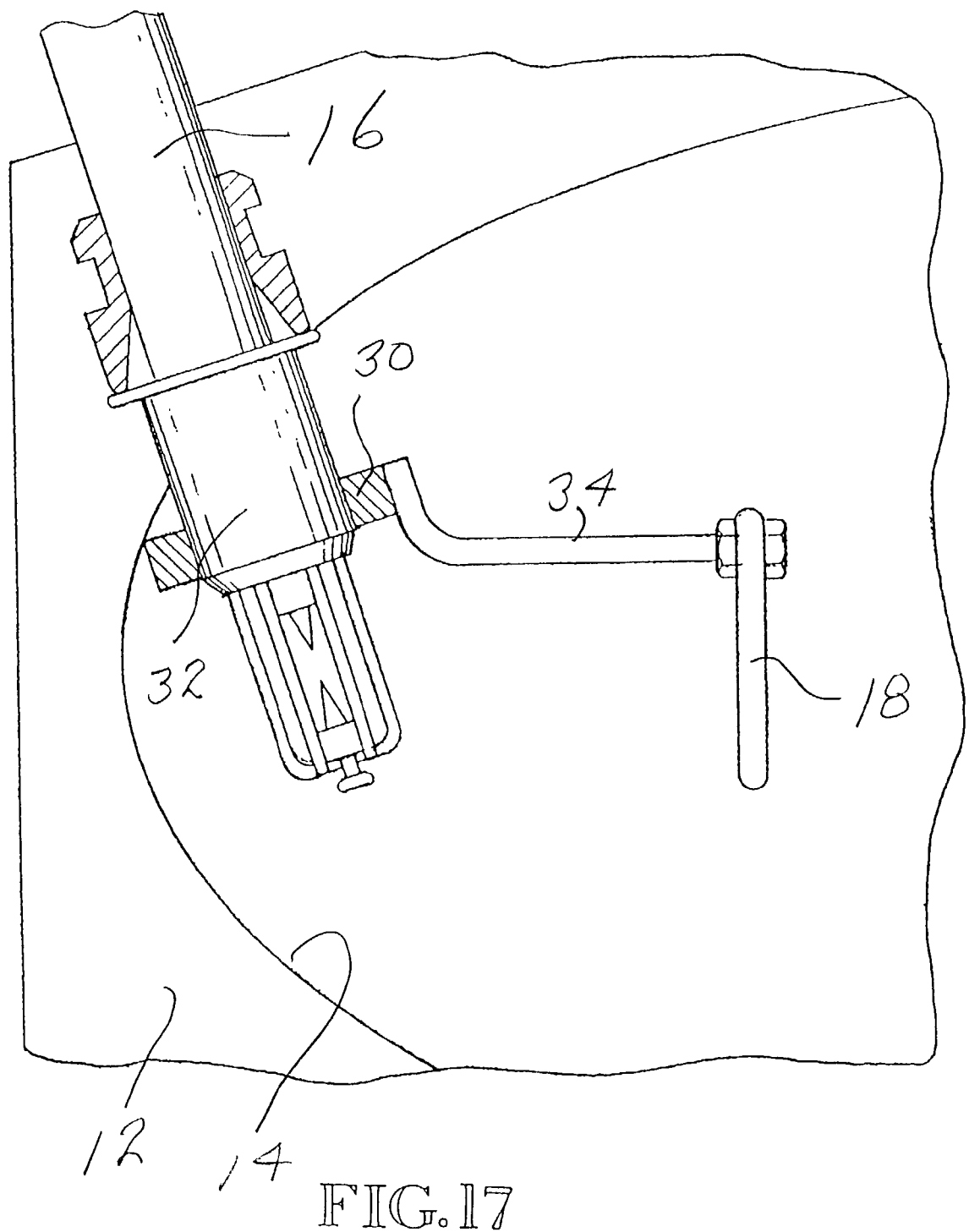
FIG. 17 is a view like FIG. 1, but with a suppressor disk added, such view showing the suppressor disk mounted on a portion of the shock-wave generator.

As an alternative, the disk suppressor 18 can be mounted directly to the shock wave source 16, as shown by FIG. 17. For lithotripsy, the source is a sparker unit 16 inserted into a reflector housing 12. A mounting ring 30 of suitable construction may surround a cylindrical housing 32 that is a part of the shock wave generator 16. Mounting ring 30 is secured in any suitable fashion against movement relatively along the housing portion 32. One or two rods 34 extend from the ring 30 to the disk 18. It is attached to the disk 18, either by weld, or by screws, or by some other method. Other mountings for shock wave devices can be designed and built relatively inexpensively. The only necessary criteria is that the mounting be such that the direct wave is blocked, and the focused wave is minimally affected.

The suppressor disk operates by blocking the direct wave as the wave propagates outward. Its influence on the main shock wave is negligible because the main shock wave is focused by the surrounding reflector, and only a very small portion of the focused wave is interfered with. Because its location is nearby the shock wave source, it is probable that for safety reasons, the suppressor should be replaced often. The main criteria for replacement will be the physical state of the device (Is it sturdy? Are the connectors still securely holding the unit in place?). In addition, if there are many pits and marks on the suppressor, it should be replaced, because one does not wish to accidentally break off a piece of the device during its operation.

The shock wave suppressor disk 18 can be utilized in any focused shock wave therapeutic device now being used, including lithotripters and other therapeutic devices. Our disk suppressor will reduce the time necessary for procedures, and thus will reduce the cost of a procedure. Furthermore, because the procedure time is shortened, there will be less harmful effects on healthy tissue.

The treatment of kidney stones is not the only use of the shock-wave focusing device of the invention. It can also be used for shock-wave therapy to treat ailments from tendonitis to sprains, and general aches that commonly occur with athletes, both human and animal. Actually, any shock-wave device that uses focusing reflectors should benefit from this invention.

Figure 15:
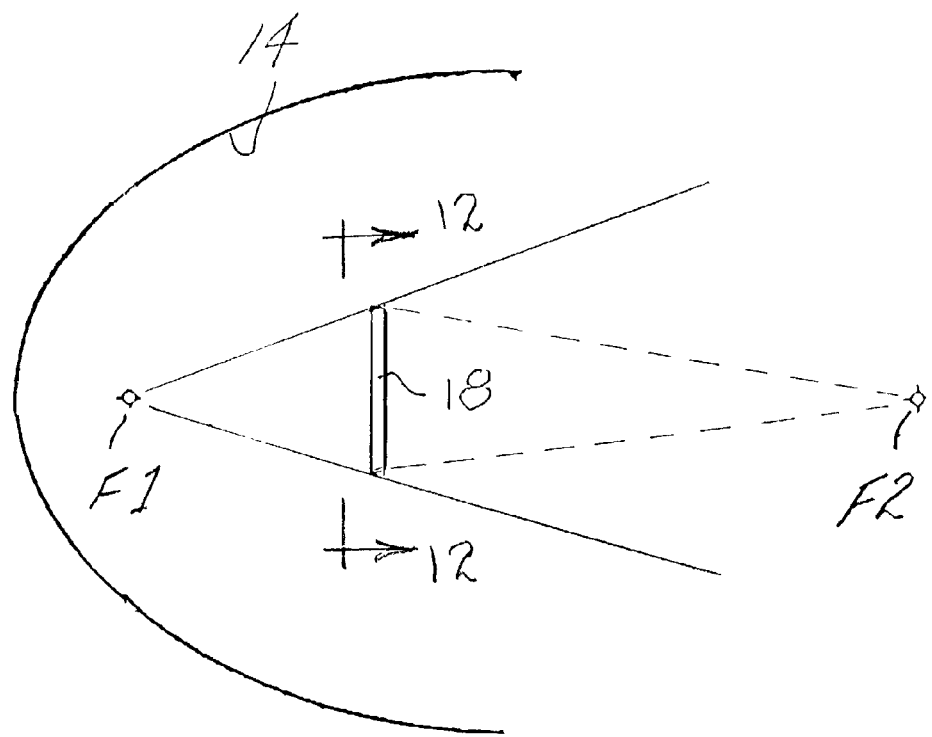
FIG. 15 is a diagram showing a broken line showing of how the direct wave intercepted by the suppressor disk would be focused if the suppressor disk had a smooth edge.

FIG. 15 shows a disk 18 positioned between the two foci F1, F2. If disk 18 were to have a circular periphery, it would cause diffraction enhancement to the outgoing wave. This is shown by the broken line 26. Note that the lines 26 represents a conical envelope that focuses towards F2, something that is not desirable. The irregularly-shaped disk 18 prevents this diffraction enhancement.

The illustrated embodiments are only examples of the present invention and, therefore, are non-limitive. It is to be understood that many changes in the particular structure, materials and features of the invention may be made without departing from the spirit and scope of the invention. By way of further example, the shock wave focusing device may be a STORTZ Lithotripter. This particular device first generates and then focuses electromagnetic energy. Direct waves can be blocked by positioning a suppressor disk endwise outwardly from the end of the cylinder. In this position it will block direct waves and increase the efficiency of the lithotripter. Therefore, it is my intention that my patent rights not be limited by the particular embodiments illustrated and described herein, but rather are to be determined by the following claims, interpreted according to accepted doctrines of patent claim interpretation, including use of the doctrine of equivalents and reversal of parts.

What is claimed is:

1. In a shock-wave device comprising a shock-wave generator and a focusing reflector configured to receive shock-wave energy direct it on a target, and wherein direct waves travel from the shock-wave device directly towards the target, the improvement comprising:
   a direct-wave cavitation suppressor in a position to block direct shock waves from traveling from the shock-wave generator directly to the target, said direct-wave cavitation suppressor being generally in the form of a disk having an irregular periphery spaced inwardly from the focusing reflector, said periphery being shaped to substantially prevent diffraction enhancement of the direct wave as it moves around the direct-wave cavitation suppressor.

2. The shock-wave device of claim 1, wherein the focusing reflector includes a reflecting surface that is substantially shaped like an end portion of an ellipsoid.

3. The shock-wave device of claim 1, wherein the shock-wave generator is an electrical spark discharge device.

4. The shock-wave device of claim 3, wherein the focusing reflector includes a reflecting surface that is shaped substantially like an end portion of an ellipsoid.

5. A method of producing a focused shock wave and delivering it to an object, comprising:
   providing a focusing reflector;
   positioning a shock-wave generator in the reflector;
   placing an object in a position to receive a focused shock wave;
   operating the shock-wave generator to discharge shock-wave created energy outwardly from itself;
   using said focusing reflector to receive shock-wave energy and focus it and direct it as a focused wave on the object;
   positioning a direct-wave cavitation suppressor with an irregular periphery in a position to substantially block direct shock waves from traveling directly from the shock-wave generator to the object, and prevent diffraction enhancement of the direct shock waves as they move around the direct-wave cavitation suppressor.

6. The method of claim 5, comprising providing a focusing reflector that is shaped substantially like an end portion of an ellipse.

7. The method of claim 5, comprising using a shock-wave generator in the form of an electrical spark discharge device.

8. The method of claim 7, comprising providing a shock-wave generator that is shaped substantially like an end portion of an ellipsoid.

* * * * *

UNITED STATES PATENT AND TRADEMARK OFFICE
CERTIFICATE OF CORRECTION

PATENT NO. : 7,033,328 B2 Page 1 of 1
APPLICATION NO. : 10/266874
DATED : April 25, 2006
INVENTOR(S) : T.J. Matula et al.

It is certified that error appears in the above-identified patent and that said Letters Patent is hereby corrected as shown below:

| COLUMN | LINE | ERROR |
|---|---|---|
| 8 (Claim 1, | 14 line 3) | after "shock-wave energy" insert --from the shock-wave generator and focus it and-- |

Signed and Sealed this

Fourteenth Day of November, 2006

JON W. DUDAS
*Director of the United States Patent and Trademark Office*

UNITED STATES PATENT AND TRADEMARK OFFICE
CERTIFICATE OF CORRECTION

| | |
|---|---|
| PATENT NO. | : 7,033,328 B2 |
| APPLICATION NO. | : 10/266874 |
| DATED | : April 25, 2006 |
| INVENTOR(S) | : T.J. Matula et al. |

Page 1 of 1

It is certified that error appears in the above-identified patent and that said Letters Patent is hereby corrected as shown below:

| COLUMN | LINE | ERROR |
|---|---|---|
| 1 | 4-6 | "The subject invention was made under DARPA contract no. N00014-99-1-0793, managed by ONR, and developed under NIH grant P01 DK 43881-09." should read --This invention was made with US Government support under grant number N00014-99-1-0793 awarded by Department of the Navy/DARPA and PO1-DK-43881 awarded by National Institutes of Health. The US Government has certain rights in this invention.-- |

Signed and Sealed this

Twenty-sixth Day of December, 2006

JON W. DUDAS
*Director of the United States Patent and Trademark Office*